(12) United States Patent
Chun et al.

(10) Patent No.: US 6,608,045 B2
(45) Date of Patent: *Aug. 19, 2003

(54) STREPTOMYCES SP PRODUCING TAUTOMYCETIN AND IMMUNOSUPPRESSANT COMPRISING TAUTOMYCETIN AS ACTIVE INGREDIENT

(75) Inventors: Hyoung Sik Chun, Seoul (KR); Jong Gwan Kim, Seoul (KR); Hung Bae Chang, Ansan (KR); Seung Kee Moon, Seoul (KR); Hyeog Jin Son, Seoul (KR); Chung Il Hong, Seoul (KR); Jung Woo Kim, Seoul (KR); Nam Hyun Lyu, Pucheon (KR)

(73) Assignee: Chong Kun Dang Corporation (KR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/308,482
(22) PCT Filed: Mar. 27, 1999
(86) PCT No.: PCT/KR99/00147
  § 371 (c)(1),
  (2), (4) Date: May 17, 1999
(87) PCT Pub. No.: WO99/50388
  PCT Pub. Date: Oct. 7, 1999

(65) Prior Publication Data
US 2001/0016599 A1 Aug. 23, 2001

(30) Foreign Application Priority Data
Mar. 27, 1998 (KR) .............................. 98-10629
Mar. 27, 1998 (KR) .............................. 98-10630

(51) Int. Cl.$^7$ ................................. C12P 17/02
(52) U.S. Cl. .................. 514/99; 514/449; 514/461
(58) Field of Search .............. 514/99, 461, 449, 514/885

(56) References Cited

U.S. PATENT DOCUMENTS 4,117,118 A    9/1978  Härri et al.
4,439,443 A  * 3/1984  Giroux ....................... 424/285
5,100,899 A  * 3/1992  Calne ......................... 514/291
5,204,329 A  * 4/1993  Ackerman ................... 514/15

FOREIGN PATENT DOCUMENTS

JP      08188533    *  7/1996

OTHER PUBLICATIONS

Cheng et al., J. Antibiot. (1989), 42(1), 141–4.*
Sakuda et al., Biosci., Biotechnol., Biochem. (1995), 59(1), 133–4.*
Cheng et al., J. Antibiot. (1989), 42(1), 141–4.*
James E.F. Reynolds, et al.; Martindale The Extra Pharmacopoeia; 31$^{st}$ edition; London Royal Pharmaceutical Society, pp. 557–562 (1996).
Katari, S.R. et al., Clinical Features of Acute Reversible Tacrolimus (FK506) Nephrotoxicity in Kidney Transplant Recipients; Clinical Transplantation; vol. 11; pp. 237–242 (1997).
Wei Li, et al.; Regulation of the Nuclear Factor of Activated T Cells in Stably Transfected Jurkat Cell Clones; Biochemical and Biophysical Research Communications; vol. 219; pp. 96–99 (1996).
Sun Lee, et al.; "A Simplified Model for Heterotopic Rat Heart Transplantation"; vol. 33; pp. 438–442 (1982).

* cited by examiner

Primary Examiner—Irene Marx
(74) Attorney, Agent, or Firm—Knobbe, Martens, Olson & Bear, LLP (57) ABSTRACT

The present invention relates to Streptomyces sp. producing tautomycetin which possesses an immunosuppressive or antibacterial activities, a process for preparing tautomycetin from the said microorganism, and an immunosuppressant or immunosuppressive pharmaceutical composition comprising tautomycetin as an active ingredient which suppresses interleukin-2 production, CD69 and interleukin-2 receptor (IL-2R) expression on the cell surface, and graft rejection in the organ transplantation. The present inventors isolated a soil microorganism which produces a substance possessing antibiotic and immunosuppressive activities, and identified the said microorganism and substance as a novel Streptomyces sp. and tautomycetin, respectively. Further, the present inventors developed a method of manufacturing the tautomycetin in a large scale from the culture of the said microorganism and discovered that tautomycetin suppresses mouse mixed lymphocyte reaction(MLR) and the expression of IL-2 based on a series of experiments employing cell line transfected with a recombinant gene.

4 Claims, 4 Drawing Sheets

STREPTOMYCES SP PRODUCING TAUTOMYCETIN AND IMMUNOSUPPRESSANT COMPRISING TAUTOMYCETIN AS ACTIVE INGREDIENT

This application is the U.S. National Phase under 35 U.S.C. §371 of International Application PCT/KR99/00147, filed Mar. 27, 1999 which claims priority to Korean Applications KR 1998-10629 and KR 1998-10630, filed Mar. 27, 1998.

BACKGROUND OF THE INVENTION

1. Field of the Invention

The present invention relates to a novel Streptomyces sp. producing tautomycetin and an immunosuppressant comprising tautomycetin as active ingredient, more specifically, to Streptomyces sp. producing tautomycetin which possesses immunosuppressive or antibacterial activities, a process for preparing tautomycetin from the said microorganism, and an immunosuppressant or immunosuppressive pharmaceutical composition comprising tautomycetin as an active ingredient which suppresses interleukin-2 production, CD69 and interleukin-2 receptor (IL-2R) expression on the cell surface, tyrosine phosphorylation of the proteins related to signal transduction via T-cell receptor(TcR), in a different suppressive mechanism from that of cyclosporin A, and graft rejection in the organ transplantation.

2. Description of the Prior Art

It has been known that the effective suppression of immune response is crucial in organ transplantation because the foreign organ brings about the rejection response by the immune system of the recipient. In this regard, the advent of immunosuppressants allowed the brilliant progress in organ transplantation, the potential remedy for autoimmune diseases, and extensive studies on immune response to foreign organs.

Immunosuppressants have been developed to suppress or attenuate rejection response to foreign organs. Cyclosporin A is the most popular immunosuppressant, which is produced by *Tolypocladium inflatum*, a soil fungus (see: U.S. Pat. No. 4,117,118). Particularly, immunosuppressants have eased organ transplantation and have been suggested as a potential drug for autoimmune diseases. The immunosuppressants have revealed some drawbacks in the sense that they may have an influence, not specific to T-cells, on the normal healthy organs. For example, it has been reported that cyclosporin A has some untoward effects that cause chronic kidney disease and hypertension after heart transplantation (see: J. E. F. Reynolds, et al., Martindale The Extra Pharmacopoeia, $31^{st}$ ed., pp. 557–562, Royal Pharmaceutical Society, London, 1996). In this regard, there are strong reasons for exploring and developing novel immunosuppressants with the reduced side effects, and FK-506 was developed as one of the candidate drugs, though it also revealed some severe side effects reported previously (see: Clin. Transplantation, 11:237–242, 1997).

Under the circumstances, the present inventors, based on the significant findings that tautomycetin efficiently suppresses the expression of interleukin-2, the early event of graft rejection, tried to develop a potential immunosuppressant comprising tautomycetin for treating graft rejection and autoimmune diseases.

SUMMARY OF THE INVENTION

The present inventors have made efforts to discover a novel immunosuppressant from the soil microorganisms. As a result, the inventors isolated a microbial strain which belongs to Streptomyces sp. from the soil of Halla-mountain in Cheju island in Korea, and obtained tautomycetin from the culture of the said microorganism. Further, they found that the tautomycetin suppresses the production of IL-2, a T-cell proliferating factor, the expression of CD69 and interleukin-2 receptor on the cell surface, and inhibits tyrosine phosphorylation of the proteins related to signal transduction via T-cell receptor(TcR), in a different mechanism from that of cyclosporin A. Finally, they developed an immunosuppressant comprising tautomycetin as an active ingredient for treating graft rejection and autoimmune diseases.

The first object of the present invention is, therefore, to provide Streptomyces sp. producing tautomycetin.

The second object of the invention is to provide a process for preparing tautomycetin from the said microorganism.

The third object of the invention is to provide an immunosuppressant comprising tautomycetin as an active ingredient.

The fourth object of the invention is to provide an immunosuppressive pharmaceutical composition comprising tautomycetin and the other immunosuppressants for a combined treatment.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

The present inventors isolated a soil microorganism which produces a substance possessing antibiotic and immunosuppressive activities, and identified the said microorganism and substance as a novel Streptomyces sp. and tautomycetin, respectively. In addition, they generated mutant strains by the aid of UV irradiation to the said microorganism. Surprisingly, the inventors discovered that tautomycetin suppresses mouse mixed lymphocyte reaction (MLR) and the expression of IL-2, based on a series of experiments employing a reporter system of transfected Jurkat T cells where the expression of β-galactosidase is driven by the multiple NF-AT binding sites upstream of minimal IL-2 promoter. Further, they discovered that: tautomycetin suppresses the expression of CD69 and interleukin-2 receptor on cell surface, which is a late event, in addition to the suppression of IL-2 expression, early event of the T-cell activation, and, it specifically inhibits tyrosine phosphorylation of the proteins related to signal transduction mediated via T-cell receptor(TcR). Moreover, it was found that tautomycetin remarkably increases the survival rate of transplanted heart in the recipient by sustaining its activity efficiently.

The present invention is further described in more detail as followings.

The present inventors isolated a soil microorganism from Halla-mountain in Cheju island in Korea, producing a compound with antibiotic activity, and found that the said compound also possesses an an immunosuppressive activity. Then, the source material produced by the said microorganism was analysed by physicochemical methods and identified as tautomycetin which is represented as following(see: Antibiotics, 42:141~144(1989)).

range as cyclosporin A, and shuts down the intra-cellular signal transduction resulting in the inhibition of T-cell proliferation. It is also found that tautomycetin suppresses the expression of IL-2 more efficiently than cyclosporin A by employing a reporter system of transfected Jurkat T cells where the expression of β-galactosidase is driven by the multiple NF-AT binding sites upstream of minimal IL-2 promoter, when stimulated by phorbol-12-myristate-13-acetate(PMA), ionomycin or OKT-3, a monoclonal antibody against CD3(see: Biochem. Biophys. Res. Commun., 219:96–99, 1996). Besides, the selective inhibition of the tyrosine phosphorylation of intracellular proteins was detected by the immunoblot assay of the Jurkat T cell which was transfected with a recombinant gene fragment, CD8-ζ chimeric DNA, harboring the ecto+transmembrane domain of CD8 and endomembrane domain of CD3-ζ chain, and then stimulated by PMA and OKT-3, a monoclonal antibody against CD3.

In addition, Jurkat T cell stimulated by OKT-8 and PMA was color-developed with monoclonal antibody against CD69(anti-CD69 mAb) and monoclonal antibody against interleukin-2 receptor(anti IL-2R mAb), and analysed by the aid of flow cytometry. The results indicated that the expression of CD69 and interleukin-2 receptor(IL-2R), the late Based on the cultural characteristics described below, the microorganism was identified as a novel microorganism which belongs to Streptomyces genus. In this regard, the said microorganism thus isolated was designated as 'Streptomyces sp. CK-4412' and deposited with the Korean Collection for Type Cultures(KCTC, #52, Oun-dong, Yusong-gu, Taejon 305–333, Republic of Korea), an international depository authority as accession No. KCTC 0445BP on Mar. 21, 1998.

Further, the present inventors developed a method of preparing the tautomycetin in a large scale from the culture of the said microorganism.

The process for preparing tautomycetin from the said microorganism comprises the steps of:
  obtaining supernatant after centrifugation of culture and collecting active fractions from the supernatant by ethylacetate extraction;
  concentrating the active fractions under a reduced pressure, chloroform extraction after dissolving the concentrate in chloroform: methanol(10:1, v/v) mixture, and reconcentration; and,
  adsorption chromatography of the concentrate dissolved in acetone and elution by acetone, to give tautomycetin.

The microbial strain employed to produce tautomycetin includes all the spontaneous or artificial mutants generated from Streptomyces sp. CK-4412(KCTC 0445BP) by physical means such as X-ray, ultraviolet(UV) ray, etc., or chemical means such as N-methyl-N'-nitro-N-nitrosoguanidine, 2-aminopurine, etc.

Moreover, the present inventors performed the mixed lymphocyte reaction(MLR) while changing the concentration of tautomycetin or cyclosporin A, and discovered that tautomycetin suppresses MLR in the similar concentration event of the T-cell activation, is dramatically suppressed. Further, an injection formula comprising tautomycetin as active ingredient was employed to examine whether the tautomycetin successfully suppresses the graft rejection in the organ transplantation. In the transplantation experiment employing rats, tautomycetin sustained the activity of transplanted heart efficiently in the lower concentration range than that of cyclosporin A, when the injection formula was administered to recipient rats from the time of the transplantation surgery, which indicated that tautomycetin increases the survival rate of transplanted heart in the recipient by sustaining its activity efficiently.

The present invention is further illustrated in the following examples, which should not be taken to limit the scope of the invention.

EXAMPLE 1

Isolation and Identification of Tautomycetin-producing Microorganism

The present inventors isolated a soil microorganism from Halla-mountain, Cheju island in Korea, producing a compound with antibiotic activity, and the said compound also possesses an immunosuppressive activity. The material produced from the said microorganism was analysed by physicochemical method such as UV adsorption spectrum, infrared adsorption spectrum, $^{1}$H-NMR spectrum, $^{13}$C-NMR spectrum and mass spectrum, and it was identified as tautomycetin(see: J. Antibiotics, 42:141~144(1989)). The said microorganism was characterized and identified as follows.

1. Morphological characteristics

Microscopic examination of Streptomyces sp. CK-4412 revealed that: three to five turns of spiral was observed in aerial mycelium, while specific organelles such as sclerotia and sporangia were not observed.

2. Composition of cell wall
   L,L-diaminopimelic acid was detected.
3. Physiological characteristics
   (1) Starch hydrolysis(starch-inorganic salt agar): (+)
   (2) Melanin pigment production: (−)
4. Cultural characteristics Cultural characteristics of the tautomycetin-producing microorganism on various growth media are summarized in Table 1 below.

TABLE 1

Cultural Characteristics of the Streptomyces sp. CK-4412 on a Variety of Growth Media (incubated at 28° C. for 14 days)

| Yeast-Malt Extract Agar (ISP No. 2) | Inorganic salt-Starch Agar (ISP No. 4) |
|---|---|
| Growth: good | Growth: moderate |
| Aerial mycelium: good, bright gray | Aerial mycelium: moderate, brown-gray |
| Vegetative mycelium: brown, wrinkles | Vegetative mycelium: dark yellow |
| Soluble pigment: none | Soluble pigment: none |

| Glycerin-Asparagine Agar (ISP No. 3) | Tyrosine Agar (ISP No. 7) |
|---|---|
| Growth: moderate | Growth: moderate |
| Aerial mycelium: moderate, brown-gray | Aerial mycelium: moderate, brown-gray |
| Vegetative mycelium: white-yellow, some wrinkles | Vegetative pigment: yellow-brown |
| Soluble pigment: grey-yellow | Soluble pigment: y444ellow-white |

| Glycerin-Asparagine Agar (ISP No. 5) | Glucose-Asparagine Agar (Waksman No. 2) |
|---|---|
| Growth: moderate | Growth: moderate, flat |
| Aerial mycelium: moderate, brown-gray | Aerial mycelium: moderate, brown-gray |
| Vegetative mycelium: white-yellow, some wrinkles | Vegetative mycelium: grey-brown |
| Soluble pigment: grey-yellow | Soluble pigment: none |

| Nutrient Agar (Waksman No. 14) | Emerson Agar (Waksman No. 28) |
|---|---|
| Growth: poor, flat | Growth: moderate, wrinkles |
| Aerial mycelium: poor | Aerial growth: poor |
| Vegetative mycelium: poor, yellow-white | Vegetative mycelium: gray-yellow |
| Soluble pigment: none | Soluble pigment: white-yellow |

5. Carbon source utilization

Streptomyces sp. CK-4412 was cultured on Pridham-Gottlieb agar medium(ISP No.9) comprising various carbon sources shown in Table 2 below, at a temperature of 28° C. for 14 days, and carbon source utilization for each sugar was investigated.

Table 2: Carbon Source Utilization of Streptomyces sp. CK4412

| Carbon Source | Utilization* |
|---|---|
| No carbon source | − |
| D-glucose | ++ |
| L-arabinose | ++ |
| D-fructose | ++ |
| D-xylose | + |
| L-rhamnose | ++ |
| Myo-inositol | ++ |
| Sucrose | + |
| Maltose | + |
| D-raffinose | ++ |

*−: No growth
+: Poor growth
++: Good growth

Based on the characteristics described above, the microorganism was finally identified as a novel microorganism which belongs to Streptomyces genus. In this regard, the said microorganism was designated as 'Streptomyces sp. CK-4412' and deposited with the Korean Collection for Type Cultures(KCTC, #52, Oun-dong, Yusong-gu, Taejon 305–333, Republic of Korea), an international depository authority as accession No. KCTC 0445BP on Mar. 21, 1998.

EXAMPLE 2

Culture of Streptomyces sp. CK-4412

100 ml of a medium for seed culture(pH 6.5) containing glucose 1% (w/v), dextrin 1% (w/v), NZ-amine(type A) 0.5% (w/v), yeast extract 0.5% (w/v) and calcium carbonate 0.1(w/v) % was added to four of 500 ml Erlenmyer flask, and autoclaved at 120° C. for 15 minutes. 1 platinum loop of slant culture of Streptomyces sp. CK-4412 grown for a week was inoculated to each of four flasks and incubated under shaking at 27° C. for 3 days. Then, 10 L of culture media(pH 6.5) containing soluble starch 3% (w/v), soybean powder 1.5% (w/v), corn steep liquor 1.5% (w/v), polypeptone 0.2% (w/v), sodium thiosulfate 0.1% (w/v), calcium carbonate 0.5% (w/v), cobalt chloride 0.0001% (w/v) was aliquoted to 100 of 500 ml Erlenmyer flasks and autoclaved at 120° C. for 30 minutes. The said seed culture was transferred to the culture media in a ratio of 2% (v/v) and incubated at 27° C. for 3 days under shaking at 240 rpm. Tautomycetin was quantitatively assayed by determining antimicrobial activity with conventional agar diffusion method employing *Aspergillus niger*(ATCC 9642)as a test organism. After 3 days of culture, pH reached to 6.9 and a titer by HPLC analysis, packed mycelium volume(PMV) were 0.03 mg/ml, 23% (v/v), respectively.

EXAMPLE 3

Isolation of Tautomycetin 9.1 L of the cell culture prepared from Example 2 was adjusted to pH 9 and centrifuged to remove all the cells. The supernatant was collected and adjusted to pH 3, then centrifuged again. 4 L of ethylacetate was added to 6.5 L of supernatant and agitated, extracted for 30 minutes. The mixture was left to stand to separate ethylacetate layer which was subsequently concentrated under a reduced pressure to give 4 g of light yellow material. After the material was dissolved in chloroform:methanol(10:1, v/v) mixture, solution was transferred to a beaker, then 500 ml of chloroform and 500 ml of water were added to the beaker at once and adjusted to pH 2 while stirring. Chloroform layer was separated by leaving to stand and concentrated under a reduced pressure to obtain about 820 mg of light yellow material. The material was dissolved in acetone and applied to a column which was packed with LH-20 (Sigma Chemical Co., U.S.A.), equilibrated with acetone and eluted with acetone. Tautomycetin was traced by antimicrobial activity with conventional agar diffusion method described in Example 2 and the activity was detected in the fraction number from 31 to 41. These fractions were pooled, concentrated and dried to give 100 g of tautomycetin.

EXAMPLE 4

Antimicrobial Activity of Tautomycetin

The antimicrobial activity of tautomycetin prepared in Example 3 was measured by agar diffusion method. $1\times10^8$/ml of spore suspension of *Aspergillus niger* was mixed with glucose-yeast extract agar medium and a paper disc containing tautomycetin was put on the agar plate. After incubation for 48 hours at 28° C., minimum inhibitory concentration(MIC) was determined to be less than 1 $\mu$g/ml by the size of growth inhibitory zone, which is 10 times as strong as cyclosporin A.

EXAMPLE 5

Generation of Mutants $10^9$/ml of spore suspension from Streptomyces sp. CK-4412(KTCC 0445BP) was irradiated for 90 seconds by ultraviolet ray with an intensity of 300 $\mu$W/cm$^2$ and incubated on nutrient agar medium at 28° C. for 7 days. The productivity of tautomycetin by mutants was assayed by paper disc method described in Example 2.

EXAMPLE 6

The Suppressive Activity Against Mouse

Mixed Lymphocyte Reaction

To investigate the suppressive activity of tautomycetin for mixed lymphocyte reaction(MLR) between the lymphocytes of mice with different MHC types, $4\times10^6$ cells/ml of splenocytes of Balb/C mouse was resuspended in the medium with or without tautomycetin or cyclosporin A. As a reacting cells, $4\times10^6$ cells/ml of splenocytes of C57BL/6 mouse was resuspended in the medium with 25 $\mu$l/ml of mitomycin C, then mixed with the said cell suspension in a volume ratio of 1:1 and aliquoted to 96-well microplate by 100 $\mu$l. After the mixed cell culture was incubated at 37° C. for 72 hours, under an environment of 5% $CO_2$, [$^3$H]-thymidine was added to the plate and further incubated for 24 hours to investigate the suppressive activity against T-cell proliferation by the degree of thymidine labelling. As shown in Table 1, it was clearly demonstrated that: the tautomycetin and cyclosporin A inhibit 50% of MLR at the concentration of 43 nM, 25 nM, respectively; and, the tautomycetin suppresses T-cell proliferation at an equivalent level of cyclosporin A.

TABLE 3

The Suppressive Activity of Tautomycetin for Mouse Mixed Lymphocyte Reaction

|  | MLR (*IC$_{50}$, nM) |
|---|---|
| Tautomycetin | 43.0 |
| Cyclosporin A | 25.0 |

*IC$_{50}$: Inhibiting concentration (50%)

EXAMPLE 7

The Suppressive Activity of Tautomycetin

Against the Expression of Interleukin-2(IL-2)

EXAMPLE 7–1

The Suppressive Activity of Tautomycetin

Against the Expression of Interleukin-2

(IL-2) Stimulated by PMA and Ionomycin

The suppressive activity of tautomycetin against the expression of interleukin-2(IL-2), which plays a crucial role in the immune system, was investigated by treating T-cell proliferating factors such as phorbol-12-myristate-13-acetate(PMA) and ionomycin, which activate protein kinase C to increase the level of diacylglycerol and $Ca^{2+}$ in cells: First, to monitor the IL-2 expression level indirectly, transfected Jurkat T cells where the expression of $\beta$-galactosidase is driven by the multiple NF-AT(nuclear transcriptional activator) binding sites upstream of minimal IL-2 promoter, were employed and the cells were resuspended in RPMI medium containing 10% fetal bovine serum, 2 mM L-glutamine and 100 unit of penicillin. $1\times10^5$ of transfected Jurkat T cells were aliquoted to 96-wll microplate, and incubated for 24 hours with the 4 $\mu$M ionomycin and 64 nM PMA, while changing the concentration of tautomycetin. Then, centrifugation was carried out to harvest cells, and washed twice with phosphate-buffered saline(PBS). 150 $\mu$l of $\beta$-galactosidase detecting solution(containing 0.1% Triton X-100, 200 mM sodium phosphate, 2 mM MgCl$_2$, 100 mM $\beta$-mercaptoethanol, 1.33 mg/ml ONPG) was added to each well and incubated at 37° C. for 1 hour. 100 $\mu$l of 1M sodium carbonate was added to stop the reaction and measured the suppressive activity of tautomycetin against the IL-2 expression by spectrophotometry at a wavelength of 410 nm. As shown in Table 4, it was found that: IC$_{50}$ of tautomycetin is 0.003 $\mu$g/ml, and tautomycetin has a suppressive activity against IL-2 expression 6 times as strong as cyclosporin A.

TABLE 4

The Suppressive Activity of Tautomycetin against IL-2 Expression

|  | Concentration ($\mu$g/ml) | Suppressive Activity | *IC$_{50}$ ($\mu$g/ml) |
|---|---|---|---|
| Tautomycetin | 1 | 98 | 0.003 |
|  | 0.1 | 88 |  |
|  | 0.01 | 83.9 |  |
|  | 0.001 | 12.8 |  |
| Cyclosporin A | 1 | 98.7 | 0.02 |
|  | 0.1 | 87.6 |  |
|  | 0.01 | 24.8 |  |
|  | 0.001 | 7.4 |  |

*IC$_{50}$: Inhibiting concentration (50%)

EXAMPLE 7–2

The Suppressive Activity of Tautomycetin

Against the Expression of Interleukin-2

(IL-2) Stimulated by TcR-mediated Signalling

Monoclonal antibody OKT-3, which binds specifically to $\epsilon$-chain of T-cell receptor(TcR)-CD3 complex, induces IL-2 expression and specific T-cell proliferation by activating TcR-mediated signal transduction. In this regard, the suppressive activity of tautomycetin against the expression of IL-2 stimulated via TcR was investigated: First, 10 μg of goat anti-mouse IgG was immobilized on 96-well microplate in an ELISA coating buffer(pH 9.0) and 10 μg of monoclonal antibody OKT-3 was also immobilzed thereon. To monitor the IL-2 expression level indirectly, transfected Jurkat T cells where the expression of β-galactosidase is driven by the multiple NF-AT(nuclear transcriptional activator) binding sites upstream of minimal IL-2 promoter, were employed and the cells were resuspended in RPMI medium containing 10% fetal bovine serum, 2 mM L-glutamine and 100 unit of penicillin. $1 \times 10^5$ of transfected Jurkat T cells were aliquoted to 96-well microplate, and incubated for 24 hours in a medium containing 64 nM PMA while changing the concentration of tautomycetin. Then, centrifugation was carried out to harvest cells, and washed twice with PBS. 150 μl of β-galactosidase detecting solution (containing 0.1% Triton X-100, 200 mM sodium phosphate, 2 mM $MgCl_2$, 100 mM β-mercaptoethanol, 1.33 mg/ml ONPG) was added to each well and after 1 hour, 100 μl of 1M sodium carbonate was added to stop the reaction and measured the suppressive activity of tautomycetin against the IL-2 expression by spectrophotometry at a wavelength of 410 nm. As shown in Table 5, $IC_{50}$ of tautomycetin was $6.6 \times 10^{-9}$ μg/ml, which suggests that the suppressive activity of tautomycetin against the IL-2 expression is 100 times as strong as cyclosporin A.

TABLE 5

The Suppressive Activity of Tautomycetin against IL-2 Expression

|  | Concentration (μg/ml) | Suppressive Activity | *$IC_{50}$ (μg/ml) |
|---|---|---|---|
| Tautomycetin | $10^{-7}$ | 74.8 | $6.6 \times 10^{-9}$ |
|  | $10^{-8}$ | 46.8 |  |
|  | $10^{-9}$ | 37.5 |  |
| Cyclosporin A | $10^{-6}$ | 96.2 | $4.0 \times 10^{-7}$ |
|  | $10^{-7}$ | 0.2 |  |

*$IC_{50}$: Inhibiting concentration (50%)

EXAMPLE 8

The Selective Suppressive Activity of Tautomycetin Against the Tyrosine

Phosphorylation of Intracellular Proteins

Figure 1A:
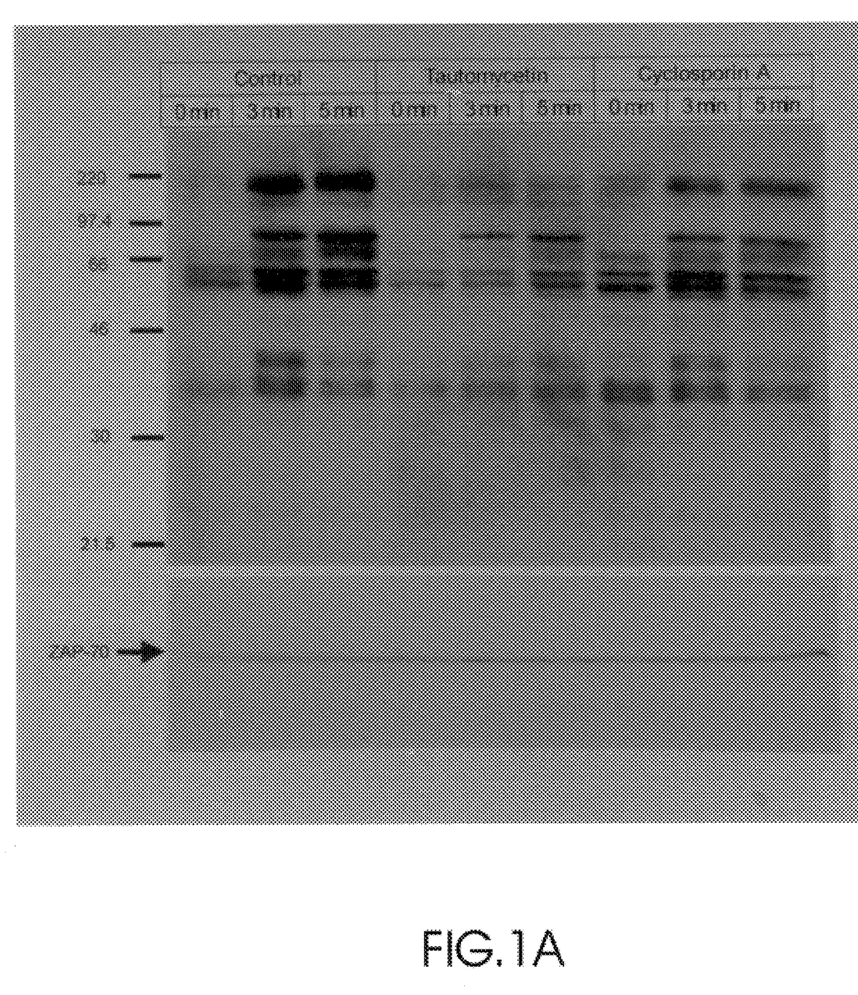
FIG. 1(A) is a photograph showing immunoblot pattern of T-cell specific inhibition of protein tyrosine phosphorylation by tautomycetin in human Jurkat T cell.
Figure 1B:
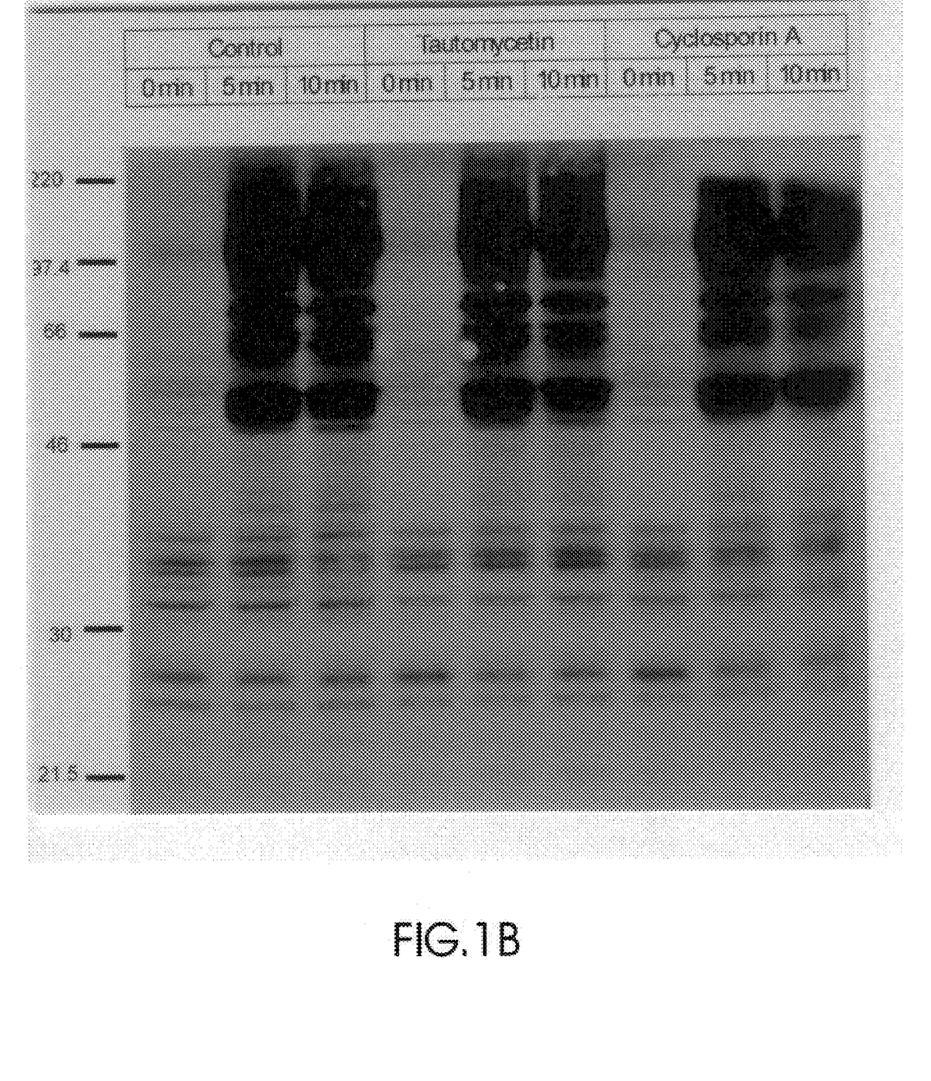
FIG. 1(B) is a photograph showing immunoblot pattern of protein tyrosine phosphorylation in human BJAB cell.

The suppressive activity of tautomycetin against the signal transduction around the membrane was investigated by determining the suppressive activity against the tyrosine phosphorylation of intracellular protein: To analyse the pathway of signal transduction mediated by TcR, Jurkat T cells which were transfected with a recombinant gene fragment, CD8-ζ chimeric DNA, harboring the ecto+transmembrane domain of CD8 and endomembrane domain of CD3-ζ chain, were cultured in RPMI medium containing 10% fetal bovine serum, 2 mM L-glutamine and 100 unit of penicillin. 1 μg/ml of tautomycetin was treated to $1 \times 10^6$ of Jurkat T cell transfectants and incubated for 10 hours, then centrifugation was carried out to harvest cells. The cells were washed twice with PBS and then stimulated by 10 μg/ml of OKT-8 and 10 μg/ml of the rabbit anti-mouse IgG antibody. The tyrosine phosphorylation was detected by immunoblot where the protein was isolated by 12.5% SDS-polyacrylamide gel electrophoresis and transferred to Immunobilon-P membrane(Millipore, U.S.A.). The phosphorylated tyrosine residue of intracellular protein or ZAP-70 protein was detected by the treatment of monoclonal antibody 4G10(Upstate Biotech Inc., U.S.A) or monoclonal antibody against ZAP-70(Zymed, U.S.A.), respectively. When the cells were stimulated by OKT-8, the tyrosine phosphorylation of various intracellular proteins which are involved in the TcR-mediated signal transduction except for ZAP-70 protein, was inhibited by the treatment of tautomycetin. As a control for the above experiment, the BJAB cell(human B-cell) which was transfected with a recombinant gene fragment, CD8-Igα or CD8-Igβ chimeric DNA, harboring the ecto+transmembrane domain of CD8, and endomembrane domain of Igα or Igβ which plays a crucial role in the signal transduction from the B-cell receptor(BcR) was employed. In a case that stimulation is given by adding monoclonal antibody against BcR, tautomycetin does not inhibit the tyrosine phosphorylation of any intracellular proteins, indicating that the tautomycetin inhibits the tyrosine phosphorylation of intracellular proteins in T-cell specific manner, which is quite different from cyclosporin A(see: FIG. 1).

EXAMPLE 9

The Suppressive Activity Against Activation-induced

Expression of Cell Surface Antigen CD69

Figure 2A:
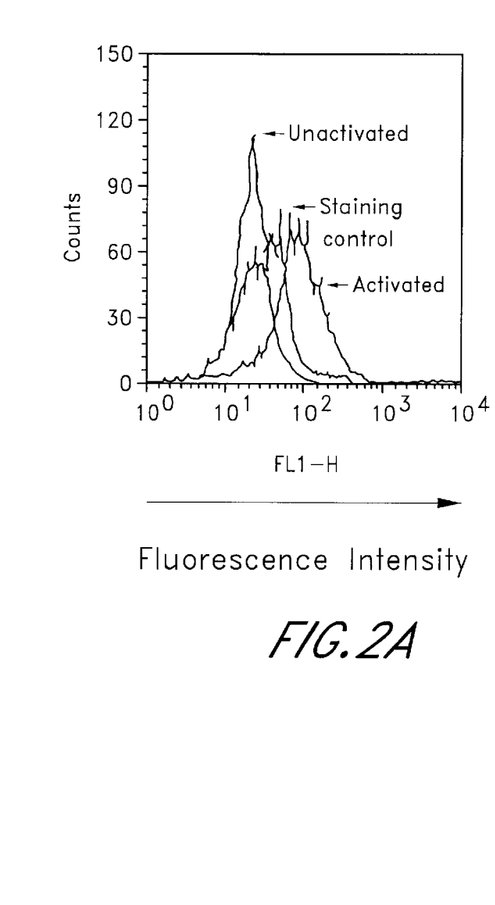
FIG. 2(A) is a graph of flow cytometry showing normal CD69 expression in human Jurkat T cells as a control.
Figure 2B:
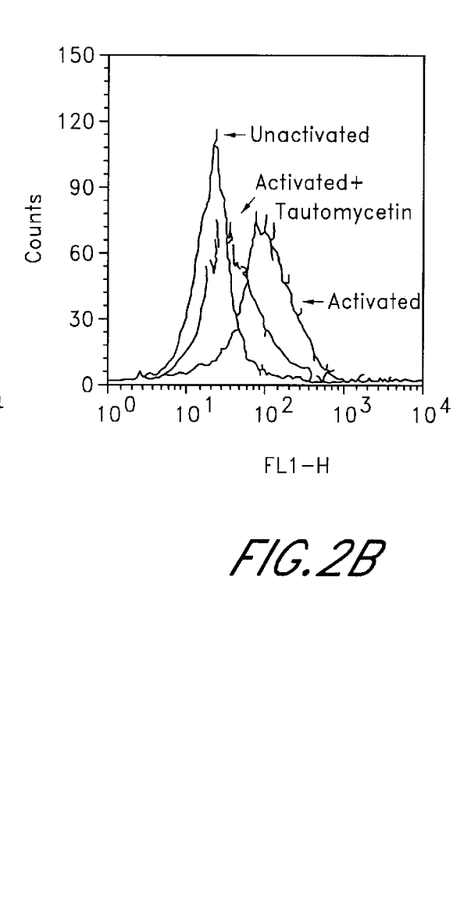
FIG. 2(B) is a graph of flow cytometry showing the inhibition of activation-induced CD69 expression by tautomycetin in human Jurkat T cells.
Figure 2C:
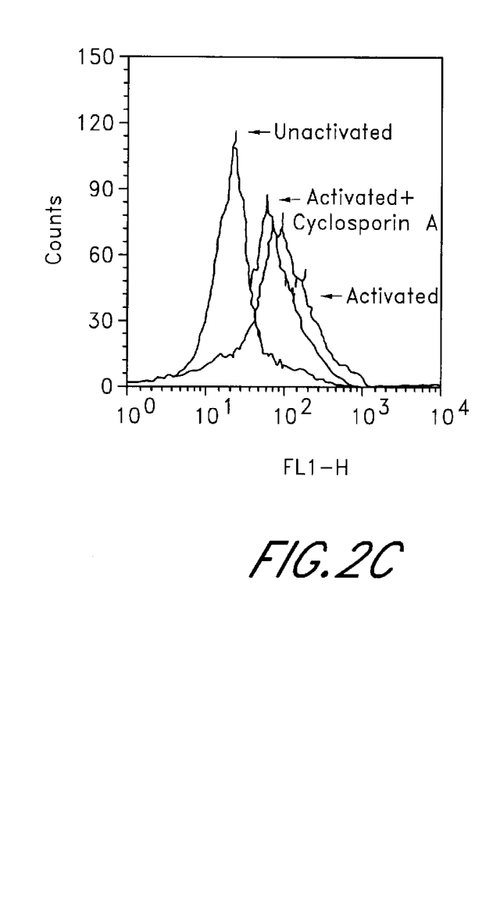
FIG. 2(C) is a graph of flow cytometry showing the activation-induced CD69 expression without existence of cyclosporin A in human Jurkat T cells.

1 μg/ml of tautomycetin was added to $1 \times 10^6$ of Jurkat T cells, which were stimulated by 10 μg/ml of OKT-3 monoclonal antibody and 50 ng/ml of PMA, and the cells were incubated for 20 hours. Monoclonal antibody against CD69 (anti-CD69 mAb) was treated to the cells to carry out color-reaction and analysed by flow cytometry. From the results, it was demonstrated that tautomycetin suppresses the expression of cell surface antigen CD69 while cyclosporin A does not, suggesting that tautomycetin has a suppressive activity distinguished from that of cyclosporin A(see: FIG. 2).

EXAMPLE 10

The Suppressive Activity Against Activation-induced

Expression of Interleukin-2 Receptor on the Cell Surface

Figure 3A:
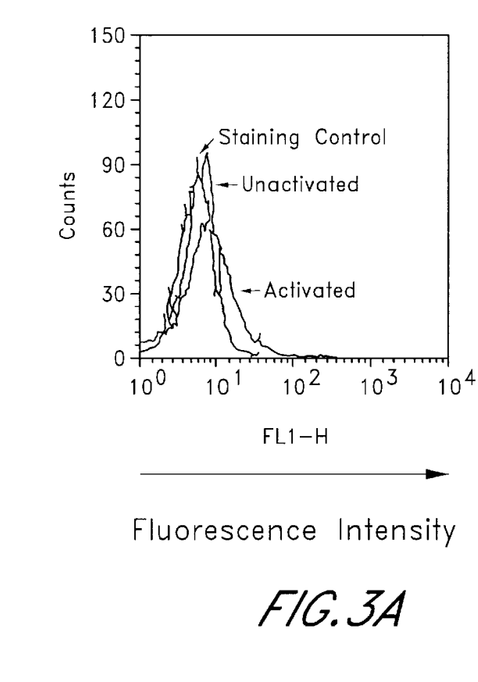
FIG. 3(A) is a graph of flow cytometry showing normal interleukin-2(IL-2) receptor expression in human Jurkat T cells as a control.
Figure 3B:
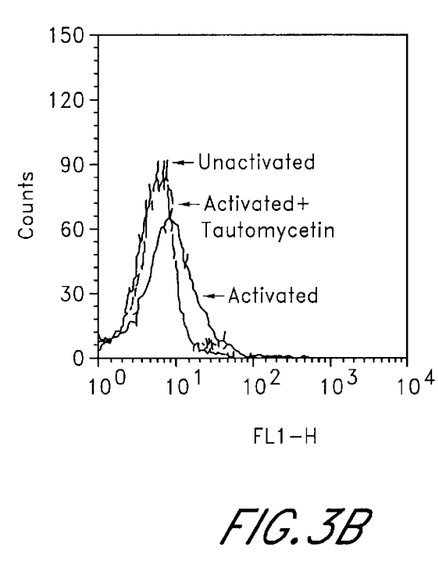
FIG. 3(B) is a graph of flow cytometry showing the inhibition of activation-induced IL-2 receptor expression by tautomycetin in human Jurkat T cells.
Figure 3C:
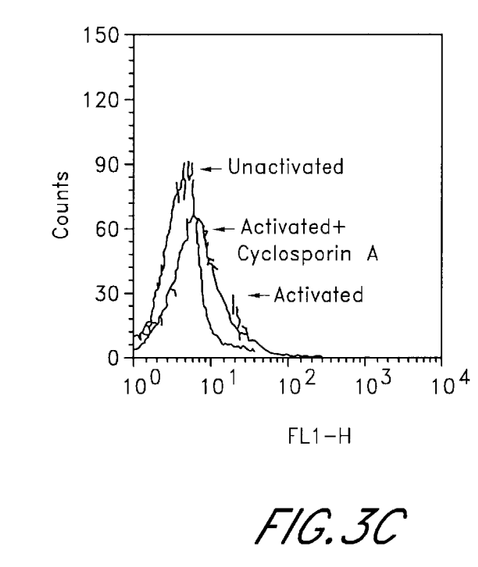
FIG. 3(C) is a graph of flow cytometry showing the inhibition of activation-induced IL-2 receptor expression by cyclosporin A in human Jurkat T cells.

To investigate the suppressive activity against interleukin-2 receptor(IL-2R) expression on the cell surface, $1 \times 10^6$ of Jurkat T cell treated with 1 μg/ml of tautomycetin was activated by OKT-3 monoclonal antibody and PMA, and color-developed by the aid of monoclonal antibody against IL-2R(anti IL-2R mAb), then analysed by flow cytometry. The results indicates that tautomycetin suppresses the expression of IL-2R on the cell surface more effectively than cyclosporin A(see: FIG. 3), suggesting that tautomycetin suppresses the expression of IL-2R in a different manner from that of cyclosporin A.

EXAMPLE 11

Preparation of an Injection Formula(I)

To prepare injection formula containing tautomycetin as an active ingredient, 25 mg of dried tautomycetin was dissolved in 0.325 ml of 95% ethanol. And then, 620 mg of Cremophor EL (BASF, Germany), a surfactant, was added and mixed to obtain transparent white-yellow material.

EXAMPLE 12

Preparation of an Injection Formula(II)

To prepare another injection formula which is improved in solubility, 20 mg of dried tautomycetin was dissolved in chloroform and transferred to a flat-bottomed vial and dried under a reduced pressure of $5 \times 10^{-4}$ torr for 4 hr. 270 µl of Cremophor RH40(BASF, Germany), a surfactant, was added and stirred for 2 hr to give an injection formula.

EXAMPLE 13

Effect of Tautomycetin on Graft Rejection in

Organ Transplantation

To investigate The effect of tautomycetin on graft rejection in organ transplantation, heart graft experiment was carried out as follows: Donor, 8 or 10 week-Lewis rat was anesthetized and its abdomen and thorax was long-sectioned. 50 units(2 ml) of heparin was percolated through inferior vena cava(IVC), and then blood-letting of inferior vena cava(IVC) and superior vena cava(SVC) were carried out in a serial manner. The physiological saline maintained at 4° C. was injected into aorta and percolated to cardiac muscle through coronary artery. Cardiac muscle, arterial pulmonary, SVC and bilateral pulmones were sectioned when the heart color changed into white, and after resection of heart, the heart was preserved in physiological saline. And then, recipient, Wistar rat was anesthetized and abdominal cavity was long-sectioned to expose abodominal aorta and IVC, then IVC and aorta were intercepted by Satinsky clamp. The aorta in the heart of recipient and the abdomen aorta of donor were continuous-sutured one-sidedly using 10–0 polypropylene thread under stereoscopic microscope. Examining the regular contraction of atrium and ventricle through ventricular fibrillation by repercolation, abdominal side was sutured continuously using silk thread(see: S. Lee et al., Transplatation, 83:438–442, 1982). The injection formula prepared in Example 11 was administered i.p. everyday to the said recipient rat, and heartbeat was examined by palpation. The time of graft rejection was defined when the heartbeat is not detected at least more than 2 times by palpation and the duration of heartbeat lasted was compared with the case of cyclosporin A. As shown in Table 6, tautomycetin sustained the heart movement at a concentration of less than 1/50 of cyclosporin A, which indicates that the said injection formula may increase the survival rate of transplanted heart when compared with the control. Therefore, it was clearly demonstrated that tautomycetin suppresses the graft rejection in heart transplantation.

After administering the injection formula prepared in Example 12 i.v. everyday from the time of transplantation, the heartbeat was examined by palpation. The time of graft rejection was defined when the heartbeat is not detected at least more than 2 times by palpation and the duration of heartbeat lasted was compared with the case of cyclosporin A. As shown in Table 7 below, tautomycetin sustains the heart movement at a concentration of less than 1/500 of cyclosporin A, which indicates that the injection formula may increase the survival rate of transplanted heart remarkably when compared with the control.

TABLE 6

The Suppressive Effect of Tautomycetin on Graft Rejection Using the Injection Formula Prepared in Example 11

|  | Dose (mg/kg) | Duration of Heart Beat (day) |
| --- | --- | --- |
| Cremophor EL (Control) | — | 7.8 |
| Tautomycetin Injection | 0.1 mg/kg | More than 50 days |
|  | 0.5 mg/kg | More than 50 days |
| Cyclosporin A Injection | 5 mg/kg | More than 50 days |

*Number of animals tested: 3

TABLE 7

The Suppressive Effect of Tautomycetin on Graft Rejection Using the Injection Formula Prepared in Example 12

|  | Dose (mg/kg) | Duration of Heart Beat (day) |
| --- | --- | --- |
| Cremophor RH-40 (Control) | — | 7.8 |
| Tautomycetin Injection | 0.01 mg/kg | More than 50 days |
|  | 0.03 mg/kg | More than 50 days |
|  | 0.1 mg/kg | More than 50 days |
| Cyclosporin A Injection | 5 mg/kg | More than 50 days |

*Number of animals tested: 3

EXAMPLE 14

Acute Toxicity Test 20 mg/kg of the injection formula prepared in Example 11, which is a dose equivalent 2000-times of effective dose described in Example 13, was administered to 10 Wistar rats via abdominal cavity for 7 days, where the rats died or injured was not examined.

Tautomycetin may be used as an active ingredient of an immunosuppressant in a free form or in a pharmaceutically acceptable salt form which is generated by adding alkali thereto, where the alkaline material includes the alkali metal (e.g., sodium or potassium) or alkali earth metal alkoxide (e.g., sodium methoxide, sodium ethoxide or potassium t-butoxide). The immunosuppressant of the invention may further comprise commercially available immunosuppressant such as cyclosporin A, FK-506, OKT-3, azathioprine and/or mizoribin, or a salt thereof, to give an immunosuppressive pharmaceutical composition for combination treatment. In addition, the pharmaceutical composition may comprise additives such as surfactants, paraplasms, coloring agents, stabilizers, buffers, suspensions, isotonics or other conventional additives, and inorganic or organic carriers to formulate solid, semi-solid or liquid-type preparations. Further, tautomycetin as an active ingredient of an immunosuppressant may be formulated for oral administration or external application. The oral formula includes, for example, coated tablets, pills, granules, soft and hard gelatin capsules, powders, fine granules, dusts, emulsions, suspensions, creams and suppositories.

The effective dose of pharmaceutical composition provided by the present invention is variable depending on the way of treatment, administration or the type of disease, the age of patient and the duration of administration. In the administration via vein and muscle, the effective dose ranges from 0.01 to 10 mg/kg for the adults weighing 60 kg, and in the case of the oral administration, the range falls into 0.1 to 50 mg/kg.

As clearly illustrated and demonstrated above, the present invention provides Streptomyces sp. producing tautomycetin, a process for preparing tautomycetin using the microorganism, and an immunosuppressant comprising tautomycetin as an active ingredient. The process for preparing tautomycetin using the microorganism and its mutants allows for a large-scale production of tautomycetin possessing antibacterial and immunosuppressive activities, which, in turn, promotes the development of antimicrobial agents and drugs for immune system-associated diseases. Since tautomycetin suppresses the expression of IL-2 which is a crucial factor in T-cell proliferation and also suppresses the graft rejection following the organ transplantation, it can be applied as a potential drug for graft rejection, graft versus host disease in the bone marrow transplantation, and autoimmune diseases such as rheumatic arthritis, multiple sclerosis, lupus erythematosus, Hashimoto's thyroiditis, myasthenia gravis, autoimmune diabetes, uveitis, asthma, etc.

What is claimed is:

1. A method for treatment of graft rejection in a mammal comprising administering tautomycetin or its pharmaceutically acceptable salt to said mammal in need of treatment of graft rejection by injection into a vein or muscle at 0.01 to 0.5 mg/kg/day.

2. The method of claim 1, wherein the salt is formed by treating alkali metal or alkali earth metal alkoxide with tautomycetin.

3. The method of claim 2, wherein the alkali metal is sodium or potassium.

4. The method of claim 2, wherein the alkali earth metal alkoxide is selected from the group consisting of sodium methoxide, sodium ethoxide, and potassium t-butoxide.

* * * * *